United States Patent
Lamb et al.

(10) Patent No.: US 10,542,759 B2
(45) Date of Patent: *Jan. 28, 2020

(54) AGRICULTURAL COMPOSITIONS AND APPLICATIONS UTILIZING ESSENTIAL OILS

(71) Applicant: Ralco Nutrition, Inc., Marshall, MN (US)

(72) Inventors: Richard Dale Lamb, Balaton, MN (US); Michael David Johnson, Balaton, MN (US)

(73) Assignee: Ralco Nutrition, Inc., Marshall, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/895,691

(22) Filed: Feb. 13, 2018

(65) Prior Publication Data

US 2018/0168170 A1    Jun. 21, 2018

Related U.S. Application Data

(63) Continuation of application No. 14/790,687, filed on Jul. 2, 2015, now Pat. No. 9,949,490.

(60) Provisional application No. 62/020,059, filed on Jul. 2, 2014.

(51) Int. Cl.
| | | |
|---|---|---|
| A01N 65/22 | (2009.01) | |
| A01N 35/02 | (2006.01) | |
| A01N 25/00 | (2006.01) | |
| A01N 25/04 | (2006.01) | |
| A01N 65/00 | (2009.01) | |
| C05D 5/00 | (2006.01) | |
| C05D 9/02 | (2006.01) | |
| C05G 3/00 | (2006.01) | |
| C05G 3/02 | (2006.01) | |

(52) U.S. Cl.
CPC .............. *A01N 65/22* (2013.01); *A01N 25/00* (2013.01); *A01N 25/04* (2013.01); *A01N 35/02* (2013.01); *A01N 65/00* (2013.01); *C05D 5/00* (2013.01); *C05D 9/02* (2013.01); *C05G 3/0064* (2013.01); *C05G 3/02* (2013.01); *Y02A 50/339* (2018.01); *Y02A 50/342* (2018.01)

(58) Field of Classification Search
None
See application file for complete search history.

(56) References Cited

U.S. PATENT DOCUMENTS

| | | |
|---|---|---|
| 4,978,686 A | 12/1990 | Sotome |
| 5,635,452 A | 6/1997 | Lulai et al. |
| 5,639,794 A | 6/1997 | Emerson et al. |
| 5,676,958 A | 10/1997 | Emerson et al. |
| 5,716,928 A | 2/1998 | Benet et al. |
| 5,741,756 A | 4/1998 | Shribbs |
| 5,759,561 A | 6/1998 | Angst et al. |
| 5,925,367 A | 7/1999 | Angst et al. |
| 6,020,287 A | 2/2000 | Brinker et al. |
| 6,069,113 A | 5/2000 | Kierzkowski et al. |
| 6,074,634 A | 6/2000 | Lopez, Jr. et al. |
| 6,159,262 A | 12/2000 | Tumbers |
| 6,313,073 B1 | 11/2001 | Farooqi et al. |
| 6,440,406 B1 | 8/2002 | Lopez, Jr. et al. |
| 6,482,455 B1 | 11/2002 | Freire et al. |
| 6,506,707 B1 | 1/2003 | Bessette |
| 6,541,042 B1 | 4/2003 | Frater-Schroder et al. |
| 6,720,352 B1 | 4/2004 | Rodriguez-Kabana et al. |
| 6,844,369 B2 | 1/2005 | Ninkov |
| 7,018,641 B1 | 3/2006 | Momol |
| 7,087,552 B2 | 8/2006 | Blowers et al. |
| 7,109,240 B2 | 9/2006 | Bessette et al. |
| 7,208,519 B2 | 4/2007 | Ninkov |
| 7,214,392 B2 | 5/2007 | D'Amelio, Sr. et al. |
| 7,255,885 B2 | 8/2007 | Lee |
| 7,429,396 B2 | 9/2008 | D'Amelio, Sr. et al. |
| 7,774,978 B2 | 8/2010 | Ding et al. |
| 7,816,410 B2 | 10/2010 | Marks |
| 7,863,350 B2 | 1/2011 | Brander et al. |
| 7,892,581 B2 | 2/2011 | Kvitnitsky et al. |
| 7,956,092 B2 | 6/2011 | Knoblauch et al. |
| 8,273,389 B2 | 9/2012 | Belkind et al. |
| 8,334,002 B2 | 12/2012 | Devisetty et al. |
| 8,425,946 B2 | 4/2013 | Green et al. |
| 8,466,087 B2 | 6/2013 | Goodwin |

(Continued)

FOREIGN PATENT DOCUMENTS

| | | |
|---|---|---|
| CN | 1647644 A | 8/2005 |
| CN | 102283842 | 12/2011 |

(Continued)

OTHER PUBLICATIONS

International Search Report and Written Opinion for International Application No. PCT/US2015/039017 dated Oct. 1, 2015, 9 pages.
"Extended European Search Report for Application No. 15814528.4, dated Oct. 18, 2017".
Motylev, et al., "The delivery of triamcinolone acetonide using emulsion-type systems", ProQuest Dissertations & Theses; Dissertation Abstracts Internatinal, vol. 65, No. 3B, Order No. AAI3126178, 2004, 1-158.
Van Der Wolf, et al., "Disinfection of vegetable seed by treatment with esssential oils, organic acids and plant extracts", Seed Science and Technology: Proceedings of the International Seed Testing Associa, Veenman, Wageningen, NL, vol. 36, No. 1, Jan. 1, 2008, 76-88.

(Continued)

*Primary Examiner* — Alton N Pryor
(74) *Attorney, Agent, or Firm* — Billion & Armitage; Benjamin C. Armitage

(57) ABSTRACT

In general, embodiments of the present invention provide seed, soil, and plant treatment compositions, and methods of making and using such products and compositions. The use of these products and compositions can act as a plant protectant and increase the growth, health, and yield of various seeds and plants such as crops and grasses, and further provide similar benefit to soils.

28 Claims, 6 Drawing Sheets

(56) References Cited

U.S. PATENT DOCUMENTS

| | | | |
|---|---|---|---|
| 8,597,395 | B2 | 12/2013 | Goodwin |
| 8,614,165 | B2 | 12/2013 | Goodwin |
| 8,642,088 | B2 | 2/2014 | Reed et al. |
| 8,808,762 | B2 | 8/2014 | Belkind et al. |
| 8,859,018 | B2 | 10/2014 | Gehin-Delval et al. |
| 9,005,644 | B2 | 4/2015 | Sims |
| 9,072,306 | B2 | 7/2015 | Sardo |
| 9,161,532 | B2 | 10/2015 | Devisetty et al. |
| 9,949,490 | B2 * | 4/2018 | Lamb .................. A01N 65/22 |
| 2004/0091558 | A1 * | 5/2004 | Lutz .................. A01N 35/02 424/745 |
| 2006/0083763 | A1 | 4/2006 | Neale et al. |
| 2008/0125321 | A1 * | 5/2008 | Rohlfsen ............. A01N 65/22 504/189 |
| 2010/0284994 | A1 | 11/2010 | Hutas |
| 2013/0005719 | A1 | 1/2013 | Hoekstra et al. |
| 2013/0028961 | A1 | 1/2013 | Vajdy et al. |
| 2013/0164361 | A1 | 6/2013 | Enan |
| 2013/0281550 | A1 | 10/2013 | Hitzfeld et al. |
| 2014/0011675 | A1 | 1/2014 | Knochenmus |

FOREIGN PATENT DOCUMENTS

| | | | |
|---|---|---|---|
| CN | 103505540 | | 1/2014 |
| CN | 102397520 | | 4/2014 |
| EP | 842606 | | 4/1998 |
| EP | 0842606 | A1 | 5/1998 |
| EP | 2684457 | A1 | 1/2014 |
| IL | 225825 | A | 6/2014 |
| JP | 2003171217 | | 1/2003 |
| NZ | 575241 | * | 10/2010 |
| WO | 2006097700 | A1 | 9/2006 |
| WO | 2010117740 | A2 | 1/2010 |
| WO | 2012072488 | A1 | 6/2012 |
| WO | 2014170893 | A1 | 10/2014 |

OTHER PUBLICATIONS

Figueroa-Espinoza, et al., "Use of grape seed tannins as emulsion stabilisers", Plant Medica, vol. 76, No. 12, Abstract, Aug. 1, 2010.

* cited by examiner

AGRICULTURAL COMPOSITIONS AND APPLICATIONS UTILIZING ESSENTIAL OILS

CROSS REFERENCE TO RELATED APPLICATION

This application is a continuation application of U.S. application Ser. No. 14/790,687, filed on Jul. 2, 2015 which claims benefit of U.S. Provisional Application No. 62/020,059, filed on 2 Jul. 2014 and which application is incorporated herein by reference. A claim of priority is made.

BACKGROUND

Pesticides or pesticidal methods, such as insecticides, are generally used to increase food production, decrease the amount of disease carrying pests, and limit human contact with such pests. Currently, the primary method of controlling such pests is through the application of pesticides containing synthetic chemical compounds. Not only are such chemicals becoming less effective at controlling and/or killing the pests, but they can also cause undesirable effects on both the environment and humans.

Initially many of the synthetic chemicals utilized as pesticides were very effective in controlling and/or killing the pests. However, after extensive usage the pests eventually build up a tolerance or resistance to some such chemicals. Once one chemical loses its utility, other synthetic chemical that the pests have not yet developed a tolerance for, are used. This cycle can result in a very large number of synthetic chemicals being released, largely unchecked, into the environment. The interaction of any synthetic chemical, let alone a number of such chemicals with the environment always comes with unexpected consequences. The non-selective way in which synthetic chemicals control pests also makes them undesirable. The chemicals can often have unexpected and serious detrimental effects on desirable insects or animals as well as the pest insect or animal. The chemicals can also contaminate areas in which humans have significant contact and cause serious effects on human health. Because of the large number of such synthetic chemicals in the environment, the interaction of such chemicals is inevitable. Often, the combined effect, often called the synergistic effect, of such chemicals can greatly outweigh their singular effects.

Furthermore, synthetic chemicals can often persist in the environment almost indefinitely. These concerns, and others, have lead the United States Environmental Protection Agency (EPA) to regulate and even ban a number of synthetic chemicals used as pesticides.

Because of the often detrimental effects of synthetic chemical pesticides and the EPA's regulatory ban of some such chemicals, a number of alternatives to synthetic chemical pesticides have been proposed and researched.

One such alternative is the use of biological organisms to control the undesired pests. Although this approach has had some significant advances and triumphs, concerns regarding the organism that is being released to control the pest will always remain. Another alternative that is seeing an increased level of interest, is the use of natural pesticides. Natural pesticides are compounds that exist in nature (e.g. in plants, animals, or other insects) and have properties that allow them to be used as is, combined, or modified to be used as pesticides.

In applications utilizing essential oils, the stability and volatilization of essential oil emulsions make their use in agriculture difficult. Certain emulsifiers are ineffective to use due to their affinity for nutrients, ultimately inhibiting the ability of the composition to deliver the intended value to a seed, plant or soil.

SUMMARY

In general, embodiments of the present invention provide seed, soil, and plant treatment compositions, and methods of making and using such products and compositions. The use of these products and compositions can act as a plant protectant and increase the growth, health, and yield of various seeds and plants such as crops and grasses, and further provide similar benefit to soils.

In general, embodiments of the present invention provide seed, soil, and plant treatment compositions, and methods of making and using such products and compositions. The use of these products and compositions can act as a plant protectant and increase the growth, health, and yield of various seeds and plants such as crops and grasses, and further provide similar benefit to soils.

In some embodiments, a seed, soil, or plant treatment composition can comprise one or more essential oils and one or more emulsifiers, wherein the one or more essential oils are present as an emulsion and the average particle size of the one or more essential oils in the emulsion is less than about 25 microns.

In other embodiments, a seed, soil, or plant treatment composition can comprise one or more essential oils one or more emulsifiers and a metal chelated compound, wherein the one or more essential oils comprise thyme essential oil, oregano essential oil, or cinnamon essential oil.

In other embodiments, a seed, soil, or plant treatment composition can comprise synthetic cinnamaldehyde and one or more essential oils from the Lamiaceae family. In one example, essential oils from the Lamiaceae family can include essential oils from the *Thymus* genus, the *Origanum* genus, or combinations thereof.

In another embodiment, a method of treating a seed, soil, or plant can comprise applying a treatment composition to one or more of a seed, soil, and a plant, wherein the treatment composition comprises one or more essential oils and an emulsifier, wherein the one or more essential oils are present as an emulsion and the average particle size of the one or more essential oils in the emulsion is less than about 25 microns.

In another embodiment, a method of treating a seed, soil, or plant to increase the health of seeds and growing plants can comprise applying a treatment composition to one or more of a seed, soil, and a plant, the treatment composition comprises one or more essential oils, wherein the one or more essential oils comprise thyme essential oil, oregano essential oil, or cinnamon essential oil, and increasing the health of seeds and growing plants can include enhancing yield, germination rate, growth, nutrient uptake and retention, drought resistance, and temporal bio-availability of nutrients in and around a seed or plant.

DETAILED DESCRIPTION

Figure 1:
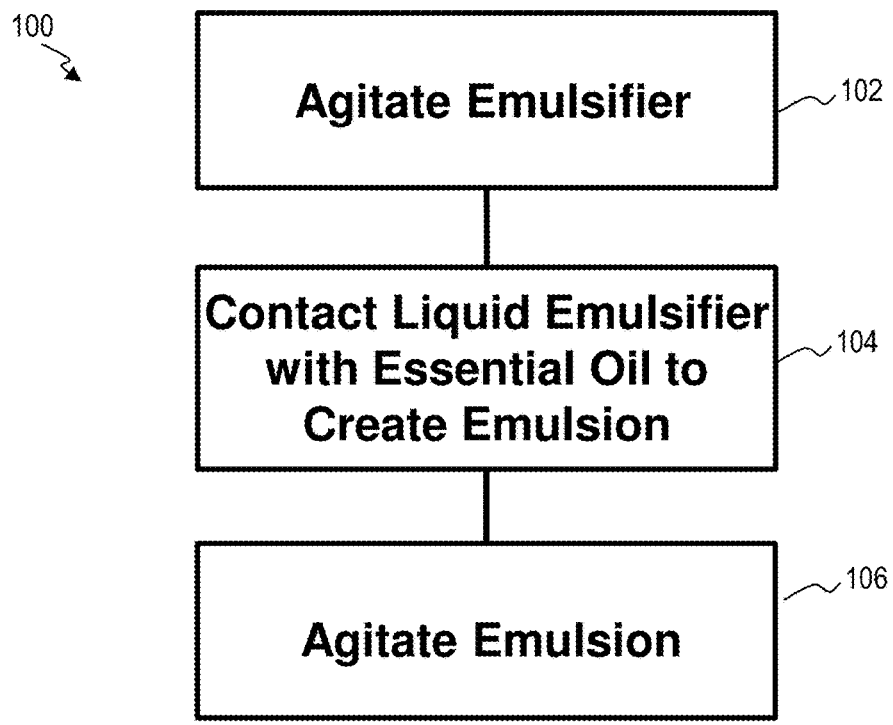
FIG. 1 illustrates a block flow diagram of a method of making an essential oil dispersion, according to one or more embodiments.

In general, embodiments of the present invention provide seed, soil, and plant treatment compositions, and methods of making and using such products and compositions. The use of these products and compositions can act as a plant protectant and increase the growth, health, and yield of various seeds and plants such as crops and grasses, and further provide similar benefit to soils. Embodiments relate to compositions including essential oils for protection of a plant seed or foliage, improvement of soil health through preferential enhancement of beneficial soil microbes, enhancement of plants' growth, yield and tolerance to adverse conditions. Such compositions including essential oils further provided incidental pesticidal benefits, which benefit treated seeds, soils, and plants. Embodiments of the present invention provide a variety of treatment compositions for enhancing the health of a seed or growing plant.

As used herein, the recited terms have the following meanings. All other terms and phrases used in this specification have their ordinary meanings as one of skill in the art would understand after review of this disclosure.

As used herein, the term "essential oils" refers to aromatic, volatile liquids extracted from plant material. Essential oils are often concentrated hydrophobic liquids containing volatile aroma compounds. Essential oil chemical constituents can fall within general classes, such as terpenes (e.g., p-Cymene, limonene, sabinene, a-pinene, y-terpinene, b-caryophyllene), terpenoids (e.g., citronellal, thymol, carvacrol, carvone, borneol) and phenylpropanoids (e.g., cinnamaldehyde, eugenol, vanillin, safrole). Essential oils can be natural (i.e., derived from plants), or synthetic. Essential oils can include one or more of African basil, bishop's weed, cinnamon, clove, coriander, cumin, garlic, kaffir lime, lime, lemongrass, mustard oil, menthol, oregano, rosemary, savory, Spanish oregano, thyme, anise, ginger, bay leaf, sage, bergamot, *eucalyptus, melaleuca*, peppermint, spearmint, wintergreen, cannibus, marjoram, orange, rose, and combinations thereof, for example.

As used herein, "plants" and "plant derivatives" can refer to any portion of a growing plant, including the roots, stems, stalks, leaves, branches, seeds, flowers, fruits, and the like. For example, cinnamon essential oil can be derived from the leaves or bark of a cinnamon plant.

As used herein "cinnamon essential oil" refers to one or more of natural cinnamon oil (i.e., essential oil derived from plants in the *Cinnamomum* genus), or synthetic cinnamon oil. Synthetic cinnamon essential oil can comprise synthetic cinnamaldehyde. Synthetic cinnamon essential oil can further comprise one or more major constituents of natural cinnamon essential oil. A major constituent is one which comprises at least 1 wt. %, at least 2.5 wt. %, or at least 5 wt. % of a natural essential oil assay.

As used herein "thyme essential oil" refers to one or more of natural thyme oil (i.e., essential oil derived from plants in the *Thymus* genus), or synthetic thyme oil. Synthetic thyme essential oil can comprise synthetic thymol. Synthetic thyme essential oil can further comprise one or more major constituents of natural thyme essential oil.

As used herein "oregano essential oil" refers to refers to one or more of natural oregano oil (i.e., essential oil derived from plants in the *Origanum* genus), or synthetic oregano oil. Synthetic oregano essential oil can comprise synthetic carvacrol. Synthetic oregano essential oil can further comprise one or more major constituents of natural oregano essential oil.

As used herein, the term "agitate" refers to exerting an outside force on a material, such as stirring, shaking, or vibrating. A vessel can be agitated by turning, tipping, shaking, etc. A paddle or stirrer can be utilized within a vessel to agitate, for example.

As used herein, the term "emulsion" refers to a system containing two or more liquids, in which at least one liquid is not substantially soluble or miscible in at least one other liquid. In an emulsion, one liquid, the "dispersed phase", is dispersed throughout a second liquid, the "continuous phase", and is often present as a fine dispersion of droplets. An essential oil may be emulsified or substantially emulsified within a carrier medium, such as water. In this example, the water is the continuous phase, and the essential oil is the dispersed phase present as a dispersion of droplets. An emulsion can optionally include an emulsifier and/or stabilizer, which can encourage the formation of the droplets by the dispersed phase, maintain the size or shape of the dispersed phase droplets, assist in reducing or reduce the size of the dispersed phase droplets, or combinations thereof. Emulsions can significantly increase the surface area of a dispersed phase. Some emulsions can further comprise dispersed insoluble particles such as solid carriers, mineral chelates, mineral salts, or the like. A low droplet size of a dispersed phase can advantageously aid in the dispersion of insoluble particles throughout the continuous phase.

As used herein, the term "emulsifier" refers to a substance that stabilizes an emulsion. The emulsifier can utilize physical properties, chemical properties, or utilize both physical and chemical properties to interact with one or more substances of an emulsion. Tannic acid is an example of an emulsifier for essential oils and water.

As used herein, the term "tannin compound" refers to a polyphenolic biomolecule including at least twelve hydroxyl groups and at least five phenyl groups. Tannin compounds include compounds utilizing gallic acid, flavone and phloroglucinol as base units. Tannic acid ($C_{76}H_{52}O_{46}$) is one form of a tannin compound. Tannic acid can include quercitannic acid and gallotannic acid, for example.

As used herein, the term "chelation" refers to the formation of two or more separate coordinate bonds between a polydentate (multiple bonded) ligand and a single central atom, typically a metal ion. The ligands are typically organic compounds, often in anionic form, and can be referred to as chelants, chelators, or sequestering agents. A ligand forms a chelate complex with a substrate such as a metal ion. While chelate complexes typically form from polydentate ligands, as used herein the term chelate also refers to coordination complexes formed from monodentate ligands and a central atom. Mineral chelated compositions include chelation.

As used herein, a "carboxylic acid" refers to organic acids characterized by the presence of a carboxyl group, which has the formula —C(=O)OH, often written —COOH or —CO$_2$H. Examples of carboxylic acids include lactic acid, acetic acid, EDTA, propionic acid and butyric acid.

As used herein, a "fatty acid" refers to a carboxylic acid, often with a long unbranched aliphatic tail (chain), which may be either saturated or unsaturated. Short chain fatty acids typically have aliphatic tails of six or fewer carbon atoms. Examples of short chain fatty acids include lactic acid, propionic acid and butyric acid. Medium chain fatty acids typically have aliphatic tails of 6-12 carbon atoms. Examples of medium chain fatty acids include caprylic acid, capric acid and lauric acid. Long chain fatty acids typically have aliphatic tails of greater than 12 carbon atoms. Examples of ling chain fatty acids include myristic acid, palmitic acid and stearic acid. A fatty acid having only one carboxylic acid group can be a ligand of a mineral.

As used herein, "lactic acid" refers to a carboxylic acid having the chemical structural formula of CH$_3$CH(OH)CO$_2$H. Lactic acid forms highly soluble chelates with many important minerals.

As used herein, an "inorganic mineral compound" or "mineral" refers to an elemental or compound composition including one or more inorganic species. For example, an inorganic mineral compound may be cobalt, cobalt carbonate, zinc oxide, cupric oxide, manganese oxide or a combination thereof. Inorganic mineral compounds may also include scandium, selenium, titanium, vanadium, chromium, manganese, magnesium, iron, nickel, copper, molybdenum, and zinc, for example. Transition metals can also be included and salts, oxides, hydroxides and carbonates of the above mentioned compounds can be suitable inorganic mineral compounds.

As used herein, "mineral chelated compound" refers to chemical compound or mixture including at least one inorganic substance and a derivative of a carboxylic acid, or reaction product of a carboxylic acid and an inorganic mineral compound. Examples of mineral chelated compounds include but are not limited to cobalt, scandium, selenium, titanium, vanadium, chromium, manganese, iron, nickel, copper, zinc, or a combination thereof chelated to one or more ligands to form a chelate (a chelate complex or coordinate complex). Examples of suitable ligands include lactate, acetate, propionate, butyrate, ethylene diamine, and EDTA.

As used herein, an "inorganic fertilizer" refers to a composition intended to enhance the growth of plants by providing macronutrients such as one or more of nitrogen, potassium, phosphorus, calcium, magnesium, and sulfur. The inorganic fertilizer typically does not include significant amounts of living organisms. Inorganic fertilizers often include micronutrients, such as boron, chlorine, copper, iron, manganese, molybdenum and zinc. Inorganic fertilizers can also include optional ingredients such as greensand or rock phosphate. The inorganic fertilizer can be, for example, an NPK fertilizer, a known commercial fertilizer, or the like.

As used herein, "biological fertilizer", "natural fertilizer" or "organic fertilizer" refers to a fertilizer that includes living organisms, or plant or animal matter. A biological fertilizer can include components such as manure, blood meal, alfalfa meal, seaweed, or compost. The fertilizers can be provided in a variety of granular or liquid forms.

As used herein, "pesticide" refers to a composition or product that kills or repels plant or seed pests, and may be broken into a number of particular sub-groups including, but not limited to, acaricides, avicides, bactericides, fungicides, herbicides, insecticides, miticides, molluscicides, nematicides, piscicides, predacides, rodenticides, and silvicides. Pesticides may also include chemicals which are not normally used as pest control agents, such as plant growth regulators, defoliants, and desiccants, or which are not directly toxic to pests, such as attractants and repellants. Some microbial pesticides may be bacteria, viruses, and fungi that cause disease in given species of pests. Pesticides may be organic or inorganic. Pesticides applied to plant seeds may remain on the surface of the seed coat following application, or may absorb into the seed and translocate throughout the plant.

As used herein, "herbicide" refers to a composition or product that kills or deters weed growth. One example of an herbicide includes glyphosate (i.e., RoundUp® herbicide).

As used herein, "insecticide" refers to a composition or product that kills or repels insects. Examples of insecticides include Sevin (carbaryl), permethrin, and *bacillus thruingiensis*

As used herein, "foliar" or "folial" refers to the foliage of a plant or crop, or applying a substance to the foliage of a plant or crop.

As used herein, "side dressing" refers to applying a substance to the soil or in a furor alongside a row of plants or planted seeds, between multiple rows of plants or planted seeds, or around a single plant or planted seed.

As used herein, "in-furrow" refers to applying a substance within a planting furrow in contact with or in near proximity to a seed. In-furrow application can occur before a seed is planted, simultaneous with seed planting, or after seed planting.

As used herein, "genetically modified plant" or "genetically modified organism" refers to an organism whose genetic material has been altered using genetic engineering techniques such as recombinant DNA technology.

As used herein, "rapidly soluble mineral chelated product" refers to a mineral chelated compound that has been altered to increase solubility in a solvent. Altering may include reducing in size, filtering, screening or chemically reacting. An inorganic mineral compound may be organically chelated such that its solubility changes from insoluble to soluble in a chosen solvent.

As used herein, "seed" refers to anything that can be sown to produce a plant. Seed can refer to an unfertilized plant ovule, a fertilized plant ovule, an embryonic plant. Seed can also refer to a whole of portion of a plant which is sown. For example, seed may refer to a whole or portion of a potato tuber.

As used herein, "solution" refers to a homogeneous or substantially homogeneous mixture of two or more substances, which may be solids, liquids, gases or a combination thereof.

As used herein, "mixture" refers to a combination of two or more substances in physical or chemical contact with one another.

As used herein, "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo. Accordingly, treating, tumbling, vibrating, shaking, mixing, and applying are forms of contacting to bring two or more components together.

As used herein, "applying" refers to bringing one or more components into nearness or contact with another component. Applying can refer to contacting or administering.

As used herein, "pre-treatment" or "seed treatment" refers to chemically and/or physically contacting seeds with a composition prior to planting or feeding.

As used herein, "reacting" refers to undergoing a chemical change. Reacting may include a change or transformation in which a substance oxidizes, reduces, decomposes, combines with other substances, or interchanges constituents with other substances.

As used herein, "filtering" or "filtration" refers to a mechanical method to separate solids from liquids, or separate components by size or shape. This can be accomplished by gravity, pressure or vacuum (suction).

As used herein, "carrier" refers to a substance that physically or chemically binds or combines with a target or active substance to facilitate the use, storage, or application of the target or active substance. Carriers are often inert materials, but can also include non-inert materials when compatible with the target or active substances. Examples of carriers include, but are not limited to, water for compositions that benefit from a liquid carrier, or diatomaceous earth for compositions that benefit from a solid carrier.

As used herein, "adherent" refers to a material, such as a polymer, that facilitates contact or binding of one or more chemicals with a seed during a seed-pre-treatment process. An example of an adherent is soluble fiber.

As used herein, "enzymes" refers to one or more biological molecules capable of breaking down cellulosic material. Enzymes include starch, proteins, non-starch polysaccharides, both soluble and insoluble, lignins and those biological molecules that facilitate chemical reactions within plants and animals.

Embodiments relate to compositions including essential oils for protection of a plant seed or foliage, improvement of soil health through preferential enhancement of beneficial soil microbes, enhancement of plants' growth, yield and tolerance to adverse conditions. Such compositions including essential oils further provided incidental pesticidal benefits, which benefit treated seeds, soils, and plants. Embodiments of the present invention provide a variety of treatment compositions for enhancing the health of a seed or growing plant. Enhancing the health of a seed or growing plant includes providing a benefit to the seed and/or plant which is distinct from a pesticidal benefit. For example, enhancing the health of a seed and/or a growing plant can include enhancing yield, germination rate, growth, nutrient uptake and retention, drought resistance, and temporal bio-availability of nutrients in and around a seed or plant. Embodiments further provide for a more consistent enhancement of these benefits throughout the lifespan of a plant. The treatment compositions can be used to improve the quality of soil. The treatment compositions can also act as microbial catalysts by providing a biological and/or physiological synergy between seeds and microbes, and between plants and microbes.

Compositions herein can act as pesticides, such as herbicides, fungicides and insecticides. Fungicides can include protectant fungicides and eradicant fungicides. For example, essential oil compositions can hinder propagation or eradicate pre-emergence and/or post-emergence pathogenic fungi. While fungal infestations are commonly cyclical (e.g., once every five years), and therefore fungicidal treatments are not theoretically required every planting year, fungicides are typically deployed in fields on a yearly basis to hedge against risk. However, such treatments can be expensive and are often detrimental to plant performance, particularly plant emergence. Therefore it is of great benefit to provide essential compositions which not only enhance plant growth and health, but also provide fungicidal properties.

Many embodiments relate to essential oil compositions that can be used to treat seeds, plants, and soil including mixtures having natural, organic, inorganic, or biological fertilizers, or combinations thereof, with one or more compatible pesticides. These compositions may also contain enzymes, fibers, water, and minerals as discussed herein. Such mixtures ensure or enhance seed germination and plant growth, health, and yield, while protecting seeds and plants from infection or infestation and harsh conditions, such as drought. Seed pre-treatment has shown to be beneficial for a number of reasons. Seed pre-treatment can create a zone of pest suppression after planting in the immediate area of the seed. As a result, fewer pesticide applications are required, which minimizes physical damage to plants, reduces application and handling costs, and cuts down on pesticide drift problems. Seed pre-treatment can allow for more accurate application of active ingredient per seed or acre. Further, seed re-treatment can require less active ingredient per seed or acre than other application methods, such as in-furrow.

For some pests, such as fungal diseases, protectant seed treatments are preferable to post-infestation or post-infection treatments because the pathogens live in such close association with host plants that it can be difficult to kill the pest without harming the host. Other types of fungicidal seed pre-treatments include seed disinfestation, which controls spores and other forms of disease organisms on the seed surface, and seed disinfection, which eliminates pathogens that have penetrated into the living cells of the seed.

Essential oil compositions as provided herein contain essential oils derived from plants (i.e., "natural" essential oils) and additionally or alternatively their synthetic analogues. Many embodiments comprise a combination of essential oils. Some embodiments comprise a combination of natural and synthetic essential oils. In some embodiments, synthetic essential oils can be a "natures equivalent" synthetic blend, which generally mimics an essential oil assay of a natural essential oil by including at least 5, at least 10, at least 15, or at least 20 of the most critical essential oils within a natural essential oil. A critical essential oil can be determined by weight percent, and/or by pharmacological efficacy. For example, a nature's equivalent synthetic oil can comprise the following constitutions as provided in Table 1:

TABLE 1

Nature's Equivalent Synthetic Thyme Essential Oil:

| Constituent | Wt. % |
| --- | --- |
| Thymol | 42.7-44.08 |
| para-Cymene | 26.88-27.09 |
| Linalool | 4.3-4.34 |
| alpha-Pinene | 4.1-4.26 |
| alpha-Terpineol | 3.14-3.14 |
| 1,8-Cineole | 2.82-3.01 |
| beta-Caryophellene | 1.98-2.27 |
| Limonene | 1.59-1.78 |
| delta-3-Carene | 1.3-1.41 |
| beta-Myrcene | 1.26-1.31 |
| Linalyl Acetate | 1.11-1.24 |
| beta-Pinene | 1.04-1.22 |
| Terpinen-4-ol | 0.96-1.14 |
| alpha-Caryophyllene | 0.71-0.71 |
| gamma-Terpinene | 0.7-0.7 |
| Sabinene | 0.37-0.5 |
| Borneol | 0.27-0.32 |
| Camphene | 0.13-0.17 |

The disclosure herein indicates the efficacy of compositions comprising a plurality of essential oils which provide a synergistic effect beyond essential oils utilized in isolation. Further, essential oil compositions provided herein do not exhibit antagonistic effect between essential oil moieties within a composition. An essential oil composition generally includes an essential oil fraction and one or more additional components. The ratio of the essential oil fraction to the one or more additional components in a composition can depend on several factors such as administration method, and the nutritional/health needs of the seed, soil, or plant to which the composition is applied, or to the consuming subject to which the composition is fed. Compositions can comprise additional components including carriers, emulsifiers, and stabilizers, among others. Compositions as provided herein can be in the form of an emulsion.

The essential oils present in some embodiments can include oils from the classes of terpenes, terpenoids, phenylpropenes and combinations thereof. The essential oils present in some embodiments can include oils of plants from the Labiatae or Lamiaceae family, and the Lauraceae family, including hybrids of plants from one or both families. Suitable essential oils from the Lauraceae family can comprise those from the *Cinnamomum* genus. Within the *Cinnamomum* genus, suitable species can include *Cinnamomum burmannii, Cinnamomum cassia, Cinnamomum camphora, Cinnamomum loureiroi, Cinnamomum mercadoi, Cinnamomum oliveri, Cinnamomum osmophloeum, Cinnamomum ovalifolium, Cinnamomum parthenoxylon, Cinnamomum pedunculatum, Cinnamomum subavenium, Cinnamomum tamala, Cinnamomum verum, Cinnamomum verum*, and hybrids thereof. The species provided in this paragraph constitute a non-limiting list of suitable species within each genus, such suitability being highlighted, in part, to lend guidance to one of skill in the art for selecting additional suitable species from each respective genus.

Suitable essential oils from the Lamiaceae family can comprise those from one or more of the *Thymus* genus, the *Origanum* genus, the *Monarda* genus. Within the *Thymus* genus, a non-limiting list of suitable species can include *Thymus caespititius, Thymus capitatus, Thymus carnosus, Thymus citriodorus, Thymus glandulosus, Thymus Herba-borana, Thymus hyemalis, Thymus integer, Thymus pseudolanuginosus* (formerly *T. lanuginosus*), *Thymus mastichinia, Thymus montanus, Thymus moroderi, Thymus pannonicus, Thymus praecox, Thymus pulegioides, Thymus serpyllum, Thymus vulgaris, Thymus zygis*, and hybrids thereof. Within the *Origanum* genus, a non-limiting list of suitable species can include *Origanum amanum, Origanum compactum, cordifolium, Origanum dictamnus, Origanum laevigatum, Origanum libanoticum, Origanum majorana, Origanum microphyllum, Origanum onites, Origanum rotundifolium, Origanum scabrum, Origanum syriacum, Origanum vulgare*, and hybrids thereof. Within the *Monarda* genus, a non-limiting list of suitable species can include *Monarda citriodora, Monarda clinopodioides, Monarda didyma, Monarda fistulosa, Monarda media, Monarda punctata*, and hybrids thereof. The species provided in this paragraph constitute a non-limiting list of suitable species within each genus, such suitability being highlighted, in part, to lend guidance to one of skill in the art for selecting additional suitable species from each respective genus.

The essential oils present in some embodiments can further include lavender essential oils from the *Lavandula* genus, Mexican bay leaf essential oils from the *Liteas* genus (e.g., *L. glaucescens*), West Indian bay tree essential oils from the *Pimenta* genus (e.g., *P. racemosa*), Indonesian bay leaf essential oils from the *Syzygium* genus, bay laurel essential oils from the *Laurus* genus (e.g., *L. nobilis*), California bay laurel essential oils from the *Umbellularia* genus (e.g., *U. californica*), lemon grass essential oils from the *Cymbopogon* genus (e.g., *C. ambiguous, C. citratus, C. flexuosus, C. martini, C. nardus, C. schoenanthus*), spearmint and peppermint essential oils from the *Mentha* genus (e.g., *M. spicata, M. piperita*), rosemary essential oils from the *Rosmarinus* genus (e.g., *R. officinalis*), sage essential oils from the *Salvia* genus (e.g., *S. sclarea*), anise essential oils from the *Pimpinella* genus (e.g., *P. anisum, P. cypria, P. major*, and *P. saxifraga*), ginger essential oils from the *Zingiber* genus (e.g., *Z. barbatum, Z. mioga, Z. officinale, Z. zerumbet*, and *Z. spectabile*), bergamot essential oils from the *Citrus* genus (e.g., *C. bergamia*), eucalyptus essential oils from the *Eucalyptus* genus, melaleuca essential oils from the *Melaleuca* genus, wintergreen essential oils from the *Gaultheria* genus (e.g., *G. antipoda, G. appressa, G. cuneata, G. depressa, G. hispida, G. hispidula, G. humifusa, G. insipida, G. lanigera, G. leschenaultii, G. mucronata, G. nummularioides, G. oppositifolia, G. ovatifolia, G. procumbens, G. rupestris, G. shallon*, and *G. trichophylla*), cannabis essential oils from the *Cannabis* genus, marjoram essential oils from the *Origanum* genus (e.g., *O. majorana*, and *O. dictamnus*), orange essential oils from the *Citrus* genus, rose essential oils from the *Rosa* genus, hybrids thereof, and combinations thereof. The species provided in this paragraph constitute a non-limiting list of suitable species within each genus, such suitability being highlighted, in part, to lend guidance to one of skill in the art for selecting additional suitable species from each respective genus.

In some embodiments, an essential oil composition can include an essential oil fraction comprising two or more essential oils from the Lauraceae family and/or the Lamiaceae family. In some embodiments, an essential oil composition can include an essential oil fraction comprising two or more of cinnamon essential oil from the *Cinnamomum* genus, thyme essential oil from the *Thymus* genus, and oregano essential oil the *Origanum* genus. In a specific embodiment, an essential oil composition can include an essential oil fraction comprising cinnamon essential oil from the *Cinnamomum* genus and thyme essential oil from the *Thymus* genus. In another specific embodiment, an essential oil composition can include an essential oil fraction comprising cinnamon essential oil from the *Cinnamomum* genus and oregano essential oil the *Origanum* genus. In another specific embodiment, an essential oil composition can include an essential oil fraction comprising thyme essential oil from the *Thymus* genus and oregano essential oil the *Origanum* genus.

In some embodiments, an essential oil composition can include an essential oil fraction comprising synthetic cinnamaldehyde and one or more of thyme essential oils from the *Thymus* genus and oregano essential oil from the *Origanum* genus. In a specific embodiment, an essential oil composition can include an essential oil fraction comprising synthetic cinnamaldehyde and thyme essential oil from the *Thymus* genus. In another specific embodiment, an essential oil composition can include an essential oil fraction comprising synthetic cinnamaldehyde and oregano essential oil the *Origanum* genus. In some embodiments, oregano essential oil can comprise carvacrol. Additionally or alternatively, thyme essential oil can comprise thymol.

In some embodiments, the essential oil fraction can comprise about 1% to about 49.5% oregano essential oil, about 1% to about 49.5% thyme essential oil, and about 1% to about 49.5% cinnamon essential oil. In other embodiments, the essential oil fraction can comprise about 15% to about 42.5% oregano essential oil, about 15% to about 42.5% thyme essential oil, and about 15% to about 42.5% cinnamon essential oil. In all such embodiments, cinnamon essential oil can optionally comprise synthetic cinnamaldehyde.

In some embodiments, the essential oil fraction can comprise about 0.5% to about 99.5% oregano essential oil and about 0.5% to about 99.5% thyme essential oil. In a specific embodiment, the essential oil fraction can comprise about 25% to about 75% oregano essential oil and about 25% to about 75% thyme essential oil. In another specific embodiment, the essential oil fraction can comprise about 40% to about 60% oregano essential oil and about 40% to about 60% thyme essential oil. In one specific embodiment, the essential oil fraction can comprise about 50% oregano essential oil and about 50% thyme essential oil.

In some embodiments, the essential oil fraction can comprise about 0.5% to about 99.5% oregano essential oil and about 0.5% to about 99.5% cinnamon essential oil. In a specific embodiment, the essential oil fraction can comprise about 25% to about 75% oregano essential oil and about 25% to about 75% cinnamon essential oil. In one specific embodiment, the essential oil fraction can comprise about 50% oregano essential oil and about 50% cinnamon essential oil. In another specific embodiment, the essential oil fraction can comprise about 50% to about 80% oregano essential oil and about 20% to about 50% cinnamon essential oil. In another specific embodiment, the essential oil fraction can comprise about 60% to about 70% oregano essential oil and about 25% to about 40% cinnamon essential oil. In one specific embodiment, the essential oil fraction can comprise about 66% oregano essential oil and about 33% cinnamon essential oil. In all such embodiments, cinnamon essential oil can optionally comprise synthetic cinnamaldehyde.

In some embodiments, the essential oil fraction can comprise about 0.5% to about 99.5% thyme essential oil and about 0.5% to about 99.5% cinnamon essential oil. In a specific embodiment, the essential oil fraction can comprise about 25% to about 75% thyme essential oil and about 25% to about 75% cinnamon essential oil. In one specific embodiment, the essential oil fraction can comprise about 50% thyme essential oil and about 50% cinnamon essential oil. In another specific embodiment, the essential oil fraction can comprise about 50% to about 80% thyme essential oil and about 20% to about 50% cinnamon essential oil. In another specific embodiment, the essential oil fraction can comprise about 60% to about 70% thyme essential oil and about 25% to about 40% cinnamon essential oil. In one specific embodiment, the essential oil fraction can comprise about 66% thyme essential oil and about 33% cinnamon essential oil. In all such embodiments, cinnamon essential oil can optionally comprise synthetic cinnamaldehyde.

Many essential oil compositions comprise an essential oil fraction comprising an effective amount of carvacrol, an effective amount of thymol, an effective amount of cinnamaldehyde, an effective amount of paracymene, or combinations thereof. In an essential oil composition including an essential oil fraction comprising oregano essential oil, thyme essential oil, and cinnamon essential oil, the essential oil fraction can comprise two or more natural essential oils wherein the combined essential oils comprise at least an effective amount of carvacrol, at least an effective amount of thymol, and at least an effective amount of cinnamaldehyde. Suitable essential oils can include essential oils from the *Cinnamomum* genus, essential oils from the *Origanum* genus, essential oils from the *Thymus* genus, essential oils from the *Monarda* genus (e.g., *M. citriodora*, *M. clinopodioides*, *M. didyma*, *M. fistulosa*, *M. media*, *M. punctata*), essential oils from the *Trachyspermum* genus (e.g., *T. ammi*), essential oils from the *Nigella* genus (e.g., *N. sativa*), and combinations thereof. Other essential oils can be used such that effective amounts of carvacrol, thymol, paracymene, and cinnamaldehyde are achieved in the essential oil fraction. Such a composition comprising natural essential oils can be supplemented by one or more synthetic essential oils to achieve effective amounts of carvacrol, thymol, paracymene, and cinnamaldehyde.

In an essential oil composition including an essential oil fraction comprising two or more of oregano essential oil, thyme essential oil, and synthetic cinnamaldehyde, the essential oil fraction can comprise one or more natural essential oils and synthetic cinnamaldehyde, wherein the combined essential oils and synthetic cinnamaldehyde comprise at an effective amount of two or more of carvacrol, at least an effective amount of thymol, and at least an effective amount of cinnamaldehyde. Suitable essential oils can include essential oils from the *Cinnamomum* genus, essential oils from the *Origanum* genus, essential oils from the *Thymus* genus, essential oils from the *Monarda* genus (e.g., *M. didyma*, and *M. fistulosa*), essential oils from the *Trachyspermum* genus (e.g., *T. ammi*), essential oils from the *Nigella* genus (e.g., *N. sativa*), and combinations thereof. Still other natural essential oils can be used such that effective amounts of two or more of carvacrol, thymol, and cinnamaldehyde are achieved in the essential oil fraction.

Some essential oil compositions comprise an essential oil fraction comprising one or more of an effective amount of thymol, an effective amount of paracymene, an effective amount of carvacrol, or an effective amount of cinnamaldehyde. An effective amount of thymol can comprise at least about 5 wt. %, at least about 10 wt. %, at least about 15 wt. %, at least about 18 wt. %, at least about 20 wt. %, or at least about 25 wt. % of the essential oil fraction. In some embodiments, an effective amount of thymol can comprise up to about 10 wt. %, up to about 15 wt. %, up to about 18 wt. %, up to about 20 wt. %, up to about 35 wt. %, or up to about 50 wt. % of the essential oil fraction. An effective amount of paracymene can comprise at least about 5 wt. %, at least about 10 wt. %, at least about 15 wt. %, at least about 18 wt. %, at least about 20 wt. %, or at least about 25 wt. % of the essential oil fraction. In some embodiments, an effective amount of paracymene can comprise up to about 10 wt. %, up to about 15 wt. %, up to about 18 wt. %, up to about 20 wt. %, up to about 35 wt. %, or up to about 50 wt. % of the essential oil fraction. An effective amount of carvacrol can comprise at least about 10 wt. %, at least about 25 wt. %, at least about 40 wt. %, at least about 55 wt. %, at least about 60 wt. %, or at least about 65 wt. % of the essential oil fraction. In some embodiments, an effective amount of carvacrol can be less than 1 wt. %. An effective amount of cinnamaldehyde can comprise at least about 10 wt. %, at least about 15 wt. %, at least about 20 wt. %, at least about 25 wt. %, at least about 30 wt. %, at least about 33 wt. %, or at least about 40 wt. %, of the essential oil fraction. In some embodiments, an effective amount of cinnamaldehyde can comprise up to about 10 wt. %, up to about 15 wt. %, up to about 20 wt. %, up to about 25 wt. %, up to about 30 wt. %, up to about 33 wt. %, or up to about 40 wt. %, of the essential oil fraction.

In some embodiments, oregano essential oil can be replaced by one or more oils which include at least 45 wt. % carvacrol, at least 55 wt. % carvacrol, at least 65 wt. % carvacrol, or at least 75 wt. % carvacrol. In some embodiments, thyme essential oil can be replaced by one or more oils which include at least 30 wt. % thymol, at least 35 wt. % thymol, at least 40 wt. % thymol, or at least 45 wt. % thymol. In some embodiments, thyme essential oil can be replaced by one or more oils which include at least 30 wt. % paracymene, at least 35 wt. % paracymene, at least 40 wt. % paracymene, or at least 45 wt. % paracymene. In some embodiments, cinnamon essential oil can be replaced by one or more oils which include at least 35 wt. % cinnamaldehyde, at least 40 wt. % cinnamaldehyde, at least 50 wt. % cinnamaldehyde, or at least 75 wt. % cinnamaldehyde. Suitable sources of effective amounts of carvacrol, thymol, and/or cinnamaldehyde can include natural essential oils and/or synthetic essential oils.

Essential oil compositions can further comprise one or more of an effective amount of eugenol, or an effective amount of citronella. An effective amount of eugenol can comprise at least about 5 wt. %, at least about 7.5 wt. %, at least about 10 wt. %, or at least about 12.5 wt. % of the essential oil fraction. An effective amount of citronella can comprise at least about 5 wt. %, at least about 7.5 wt. %, at least about 10 wt. %, or at least about 12.5 wt. % of the essential oil fraction.

In some embodiments, the essential oil fraction comprises 100% of the essential oil composition. An essential oil composition can optionally comprise a carrier. Carriers are ideally inert materials which do not react with the active components (i.e., the essential oil fraction) of the composition chemically, or bind the active components physically by adsorption or absorption. Liquid carriers include water, pure water, such as reverse osmosis water, or other liquids such as crop oils or surfactants which are compatible with the composition and plant tissue. In some embodiments, the composition will be about 80% to about 99% liquid carrier, about 70% to about 99% liquid carrier, about 60% to about 99% liquid carrier, or about 40% to about 99% liquid carrier.

Solid carriers such as limestone and diatomaceous earth can be utilized. Solid carriers can be utilized for practical purposes, such as machinery used to coat seeds with essential oil compositions or distribute essential oil compositions into a field. In some embodiments the composition can be at least about 30% solid carrier by weight, at least about 55% solid carrier by weight, at least about 75% solid carrier by weight, or at least about 80% solid carrier. In some embodiments, the composition will be about 80% to about 99% solid carrier, about 70% to about 99% solid carrier, about 60% to about 99% solid carrier, or about 40% to about 99% solid carrier.

The total amount of carrier in a composition can be determined based on a ratio of one or more carriers to one or more elements within the composition. In some examples, a particular ratio or ratio range of one or more carriers to elements within the composition can be determined based on plant nutrition, growth, or other factors. In some other examples, a particular ratio or ratio range of one or more carriers to elements within the composition can be determined based on technical limitations of agricultural or processing machinery.

An essential oil composition can further comprise one or more emulsifiers. An emulsified essential oil fraction can increase the bioavailability and efficacy of an essential oil composition when in contact with a seed, soil, plant, or soil. An essential oil fraction can be combined with an emulsifier and a dry carrier, or alternatively an essential oil fraction can be combined with an emulsifier and a liquid carrier, as disclosed above, to form an emulsion. The emulsifier can be combined with an essential oil fraction in a ratio of about 3:1 to about 1:3, about 2:1 to about 1:2, about 1.5:1 to about 1:1.5, or about 1:1. An essential oil composition comprising an essential oil fraction, a liquid carrier, and an emulsifier can have an average essential oil droplet size of less than about 25 microns, less than about 15 microns, less than about 10 microns or less than about 5 microns.

An emulsifier combined with a liquid carrier can generally be referred to as a liquid emulsifier. In some embodiments, an emulsion can comprise up to about 35%, up to about 40%, up to about 45%, or up to about 50% essential oil fraction and emulsifier, with the balance comprising a liquid carrier. In some embodiments, an emulsion can comprise less than about 20%, less than about 15%, less than about 10%, about 5%, or less than about 5% essential oil fraction and emulsifier, with the balance comprising a liquid carrier. In some embodiments, an emulsion can comprise about 40% to about 60%, or about 45% to about 55% essential oil fraction and emulsifier, with the balance comprising a liquid carrier. In some embodiments, an emulsion can comprise about 1% to about 10%, about 2.5% to about 7.5%, or about 5% essential oil fraction and emulsifier, with the balance comprising a liquid carrier. In many embodiments the liquid carrier is water. The liquid carrier content can vary depending on the amount and type of emulsifier.

A suitable emulsifier is larch arabinogalactan. Other suitable emulsifiers include polydextrose, chitin, *psyllium*, methyl-cellulose, hydrolyzed guar, guar, soy polysaccharide, oat bran, pectin, inulin, Fructooligosaccharides (FOS), xanthan gum, alginate, chemically modified cellulosic, Acacia, and gum Arabic. One or more emulsifiers can be used to form an emulsion. In some embodiments, one or more emulsifiers can additionally or alternatively be used as a stabilizer. Stabilizers can be used to alter the viscosity of an emulsion. Altering a viscosity can include maintaining a viscosity, increasing a viscosity, or decreasing a viscosity.

In some embodiments, a suitable emulsifier can include a tannin compound, such as tannic acid. Tannin can be used as an alternative to or in combination with the emulsifiers described above. In some embodiments, a liquid emulsifier can comprise about 100% tannic acid, about 80% to about 95% tannic acid, about 60% to about 85% tannic acid, about 40% to about 60% or about 1% to about 50% tannic acid, with the balance being a liquid carrier.

FIG. 1 illustrates a block flow diagram of a method 100 of making an essential oil composition, such as an essential oil emulsification in an aqueous carrier, is shown, according to some embodiments. One or more liquid emulsifiers are agitated 102. The one or more liquid emulsifiers are contacted 104 with one or more essential oils, sufficient to create an emulsion. The emulsion is agitated 106 while monitoring at least an emulsion temperature.

The liquid emulsifier (i.e., water and one or more emulsifiers) is agitated 102 in a vessel, such as by stirring, for a time sufficient to produce visible motion on the surface of the one or more liquid emulsifiers. The visible motion can be from the approximate surface center to one or more surface edges, at the perimeter of the vessel, for example. The time taken to reach such visible motion depends on the type of liquid emulsifier and ratio of emulsifier to water (e.g., viscosity). Once a suitable motion is established at the surface of the liquid emulsifier, one or more essential oils are added (e.g., contacted 104). The agitation of the liquid continues and an emulsion begins to form on contact. The contact rate or addition rate should be slow enough to substantially prevent volatilization of the essential oils.

The agitation continues during the addition of the essential oils. The emulsion begins to form assuming the rate of essential oil addition is slow enough to prevent a high shear environment, adversely affecting the volatilization of the oils. Agitation 106 of the emulsion then continues until the emulsion temperature reaches about 100° F. to about 110° F., about 103° F. to about 108° F. or about 104° F. to about 107° F. As the emulsion forms, the viscosity increases. The method of agitation should be adjusted to compensate for the increase in viscosity. For example, if a stirring method is used, the stirrer or paddle should increase in force to maintain the same level of movement of the liquid as the emulsion thickens.

The final emulsion can have an average droplet size of less than about 25 microns, less than about 15 microns, less than about 10 microns or less than about 5 microns. The smaller droplet size allows for a more stable emulsion and one that previously could not be utilized for agricultural uses due to instability and high volatilization rates.

Figure 2:
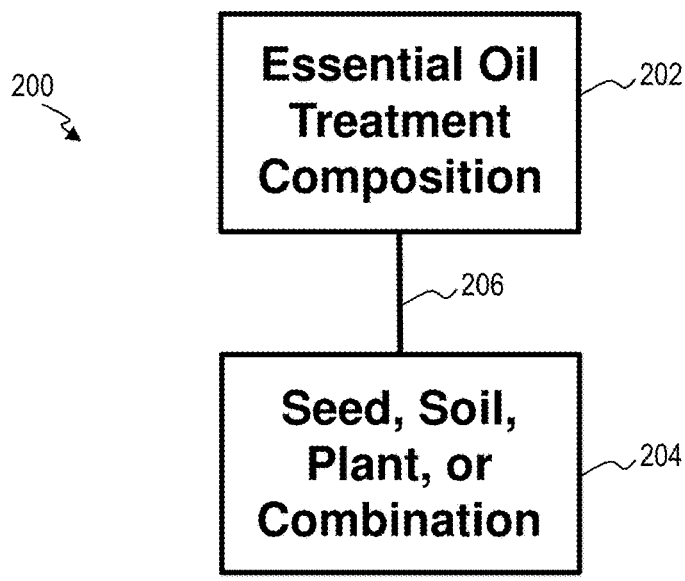
FIG. 2 illustrates a block flow diagram of a method of treating seeds, soil, plants or combinations thereof with an essential oil treatment composition, according to one or more embodiments.
Figure 3A:
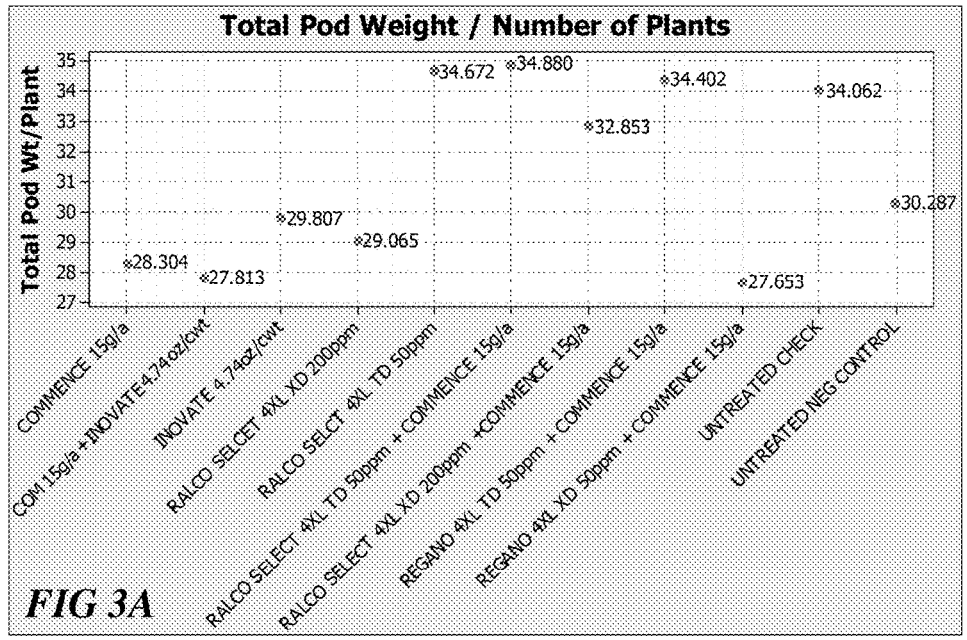
FIGS. 3A-D illustrate results from a soy bean greenhouse study using essential oil compositions, according to one or more embodiments.
Figure 3B:
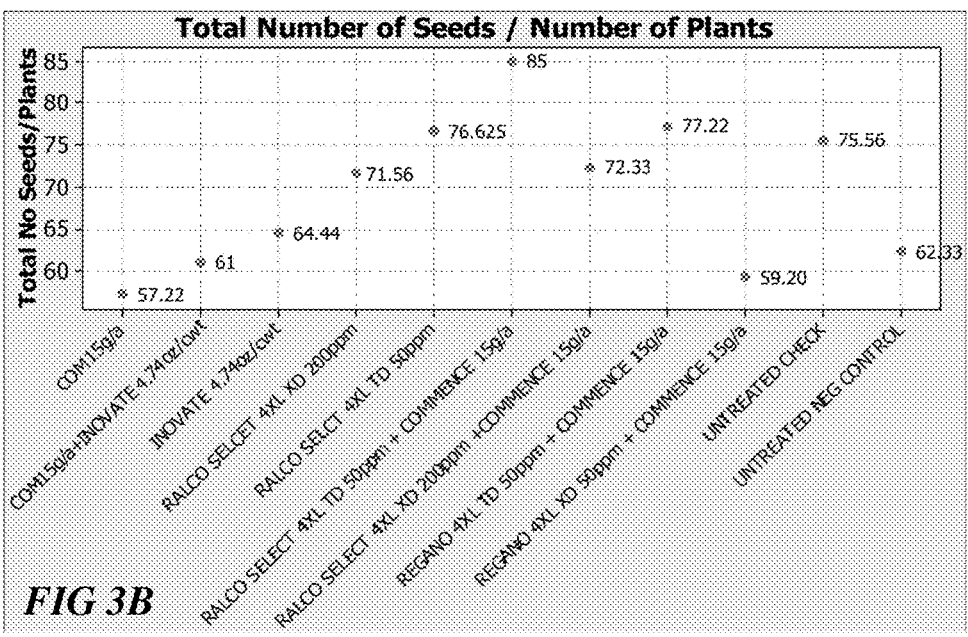
Figure 3C:
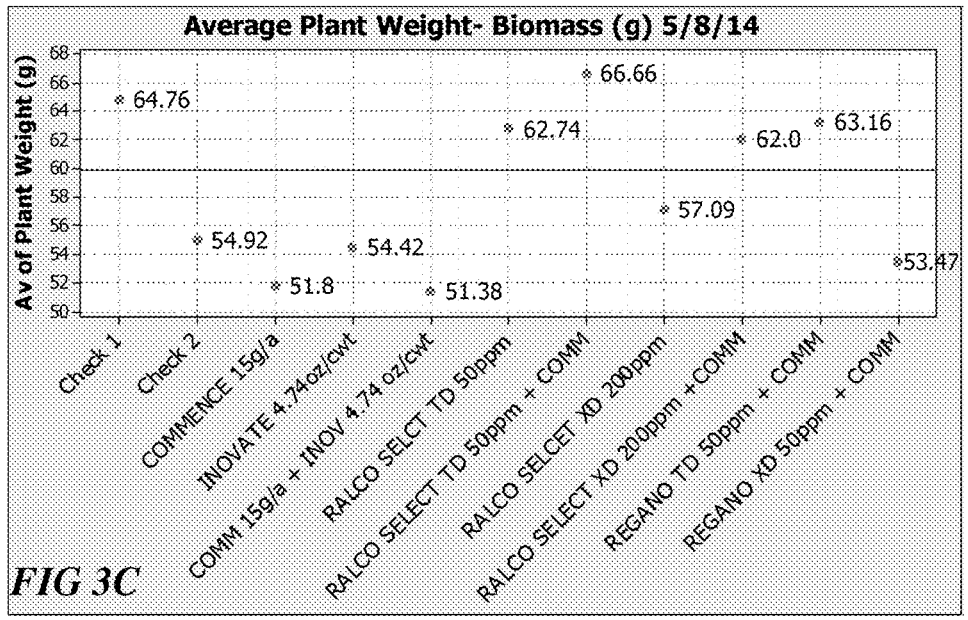
Figure 3D:
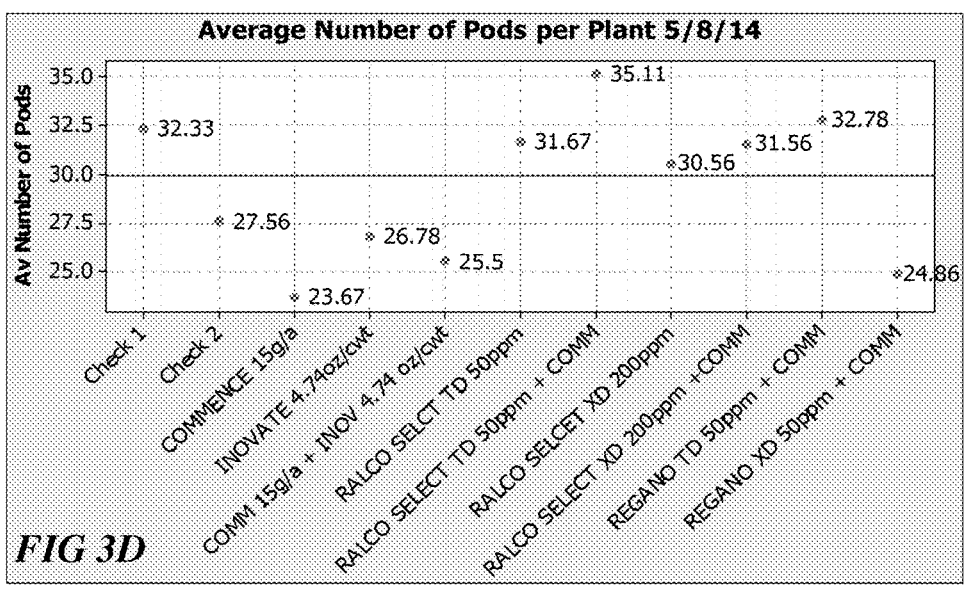

Referring to FIG. 2, a method 200 of treating seeds, soil, plants or combinations thereof with an essential oil treatment composition is shown, according to one or more embodiments. An essential oil treatment composition 202 can be applied 206 to one or more of seeds, plants and soil 204.

The essential oil treatment composition 202 can include one or more essential oils and one or more emulsifiers. The one or more emulsifiers can include arabinogalactan, at least one tannin compound, such as tannic acid, and combinations thereof. The average particle size of the composition can be less than about 25 microns, less than about 15 microns, less than about 10 microns or less than about 5 microns. The tannin compound, such as tannic acid, provides better stability, anti-microbial properties and stabilizing characteristics than traditional essential oil emulsifiers. Although a stabilizer can be used, such as xantham gum or guar gum, the use of tannic acid as an emulsifier renders such previously required stabilizers as optional at best. The composition also provides a carrier, such as water.

The amount of essential oil applied to seed, soil or plant depends on a number of factors including application (a higher amount can be applied to soil than a seed, for example), purpose (i.e., animal deterrent versus plant protectants), and overall composition components. As a seed treatment (pre-treatment), the amount of essential oil may be about 50 ppm to about 200 ppm on a seed to be planted. The amount of essential oils may be about 0.1% to about 10% of a complete product, including mineral compounds, carriers, fibers, etc. In foliar applications, the amount of essential oil applied can be about 0.0001% to about 0.005% of an application or up to about 50 ppm on a plant, due to potential damage to plant tissue. Side dressing, in-furrow or soil applications can be up to about 20% of a product. In addition, the aromatic concentration can be increased for soil applications intentionally to deter animals, such as deer from approaching crops or feed plots (at least until desired).

Treatment methods include direct seed treatment, folial, side-dressing, and in furrow. Direct seed treatment methods can be accomplished away from a planting site, at a planting site, and during planting. For example, seeds can be contacted with a seed treatment during planting. Direct seed treatment can provide advantages over folial and in furrow treatment methods by reducing wasted active ingredients and thereby the overall amount of necessary or sufficient treatment product for a given seed lot or acreage. Additionally, direct seed treatment formulations can be more concentrated than formulations directed to folial and in furrow treatment methods. In some cases this is because formulations directed to folial and in furrow treatment methods have a higher percentage of carrier material. The more highly concentrated direct seed treatment formulations therefore also provide advantages as they are more easily transported, and additionally or alternatively do not require facilities and equipment for mixing the formulations with carriers or other elements. Seed treatment methods can also reduce damage to plants caused by some methods of folial, side-dressing, and in-furrow application methods, and can further reduce energy usage and equipment required by the same.

Seed pre-treatment pesticides can be applied as dusts, but are often homogeneous solutions or heterogeneous slurries or suspensions. Seed treatment or pre-treatment 106 can be accomplished within a seed bag or by mechanical means, such as in a tumbler. The one or more seeds can be agitated after applying. Agitating can include tumbling, vibrating, mixing, shaking, and combinations thereof. The applying can be accomplished by spraying, pouring or other means of contacting the essential oil composition and seeds. Seed pre-treatment can be carried out at an off-site facility, on-site at the farm, or on-board planting equipment immediately prior to planting.

The essential oil composition can be combined with one or more pesticides, including herbicides, insecticides, fungicides, and adherents, including commercial products, without negatively affecting the commercial product or seeds. Although the essential oils emulsified provide exceptional adherence to seeds and plants, an additional adherent can optionally be utilized, such as a polymer (e.g., polysaccharide).

The treatment compositions described herein can be beneficial to a variety of seeds, plants, and soils. The compositions can be particularly beneficial to crops and grasses, and for improving the health of soil used for crops and grasses. Examples of crop plants that benefit from treatment with the compositions described herein include, but are not limited to, corn, alfalfa, beans, sugar beets, potatoes, wheat, fruits, oats, cotton, rice, soy, and the like. Additionally, GMO variants of the above and other plants can be strengthened and benefit from the embodiments of the present invention.

Examples of grasses that benefit from treatment with the compositions described herein include, but are not limited to, lawn grasses, turf grasses such as grass for sports fields and greens. Specific examples include Kentucky bluegrass, annual bluegrass, clover, Bermuda grass, bentgrass, ryegrass, Indian ricegrass, jointed goatgrass, purple three-awn grass, downy brome, common rye, and the like.

The composition can additionally include a variety of minerals, either as chelates or compounds, such as salts. The chelates can be any suitable and effective chelate described herein. Examples of mineral chelated compounds include a cobalt chelated compound, a scandium chelated compound, a selenium chelated compound, a titanium chelated compound, a vanadium chelated compound, a chromium chelated compound, a manganese chelated compound, an iron chelated compound, a nickel chelated compound, a copper chelated compound, a zinc chelated compound, or a combination thereof. The chelated portion may include lactate, ethylene diamine, ethylenediamine tetraacetate (EDTA), propionate, butyrate, acetate and combinations thereof. Examples of a chelated mineral compound include mineral lactate compound, a mineral propionate compound, a mineral butyrate compound, a mineral EDTA compound, a mineral acetate compound, or a combination thereof.

One specific, non-limiting example of a chelated compound is organically chelated cobalt, for example, having the chemical formula: $(CH_3—CH(OH)COO^-)_2$—Co which can be shown as:

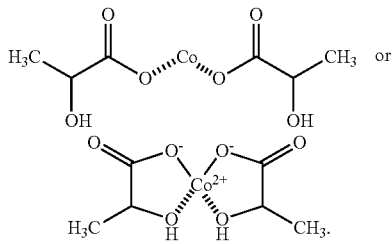

The minerals of the mineral chelated compounds include aluminum, scandium, selenium, titanium, vanadium, chromium, magnesium, manganese, cobalt, iron, nickel, copper, tin, zinc, molybdenum. For example, the cobalt, iron, manganese, copper, and zinc can be lactates, EDTA complexes, or sulfates, and the molybdenum can be hydrated molybdic acid.

Salt compounds can include aluminum, scandium, selenium, titanium, vanadium, chromium, magnesium, manganese, cobalt, iron, nickel, copper, tin, zinc, molybdenum. Salt anions can include bromide, chloride, fluoride, carbonate, hydroxide, nitrate, oxide, phosphate, sulfate, formate, acetate, propionate, butyrate, oxalate, citrate, malate, lactate, or tartrate.

The composition can also include a fiber, for example, a fiber that can act as a food source for beneficial bacteria in soil or another growth medium. Fiber can also act as an adherent. Soluble fibers are preferred as they generally enhance product efficacy and stability by keeping less soluble materials in solution or suspension due to their inherent charge and ability to disperse other charged components in solution. Soluble fibers also allow for higher composition-to-seed adhesion in pre-treatment. Fiber content within the composition is adjustable to better maintain less soluble materials in solution or suspension, and to modify composition "stickiness" or adhesion properties. Higher fiber content and "stickiness" is often desirable in seed pre-treatments in order to ensure sufficient composition binding to and coverage of the seeds.

Fiber content and type can also be modified to control composition-seed adhesion time, and adhesion strength. Because seeds can be pre-treated off-site and must be transported to farms, adhesion strength is important to ensure that pre-treatment compositions do not shake, rub, or fall off the seeds during processing, shipping, storage, or planting. The higher fiber content and overall concentration of pre-treatment compositions in comparison foliar, side dressing, and in-furrow application compositions may increase composition density. Lower fiber content may be preferable for liquid foliar, side-dressing, or in-furrow application compositions, which ideally have lower percent solids and viscosities to allow for easier transport and application, and to minimize equipment clogging. Suitable and effective fibers include hemicellulose, for example, the hemicellulose extracted from Larch trees. Another example of a suitable fiber is a *yucca* plant extract, commercially available as Saponix 5000 or BioLiquid 5000.

The composition can further include one or more enzymes, including a blend of enzymes. The enzymes can serve to break down cellulosic material and other material, including stover left on a field after harvest. Useful and beneficial enzymes include enzymes which break down starch, such as amylases, enzymes which break down protein, such as proteases, enzymes which break down fats and lipids, such as lipases, and enzymes which break down cellulosic material, such as cellulases. Enzymes can be provided within the compositions described herein, for example, to facilitate a degradation of cellulosic material in and/or around a seed, soil, or plant.

The composition can also include one or more compatible herbicides, such as glyphosate. The composition can include many different types of fungicides, which may contain active ingredients including but not limited to: chlorothalonil, copper hydroxide, copper sulfate, mancozeb, flowers of sulfur, cymoxanil, thiabendazole, captan, vinclozolin, maneb, metiram, thiram, ziram, iprodione, fosetyl-aluminum, azoxystrobin, and metalaxyl.

The composition can include many different types of insecticides, which may contain active ingredients including but not limited to: aldicarb, acephate, chlorpyrifos, pyrethroids, malathion, carbaryl, sulfuryl fluoride, naled, dicrotophos, phosmet, phorate, diazinon, dimethoate, azinphosmethyl, endosulfan, imidacloprid, and permethrin.

The composition can include many different types of herbicides, which may contain active ingredients including but not limited to: diuron, 2-methyl-4-chlorophenoxyacetic acid (MCPA), paraquat, dimethenamid, simazine, trifluralin, propanil, pendimenthalin, metolachlor-S, glyphosate, atrazine, acetochlor, "2,4-D", methylchlorophenoxypropionic acid (MCPP), pendimethalin, dicamba, pelarganoc acid, triclopyr, monosodium methyl arsenate (MSMA), sethoxydim, quizalofop-P, primisulfuron, imazamox, cyanazine, bromoxylin, s-ethyl dipropylthiocarbamate (EPTC), glufosinate, norflurazon, clomazone, fomesafen, alachlor, diquat, and isoxaflutole.

In one embodiment, the composition is prepared to provide high percentages of aqueous soluble minerals. Additional optional components include forms of soluble calcium, boric acid, and the like.

In some embodiments, the composition includes a general mineral complex, including one or more mineral chelated compounds (e.g., cobalt chelated compound), and one or more organic or inorganic mineral salts (e.g., cobalt sulfate). The mineral chelated compound can include one or more of a cobalt chelated compound, scandium chelated compound, selenium chelated compound, titanium chelated compound, vanadium chelated compound, chromium chelated compound, manganese chelated compound, iron chelated compound, nickel chelated compound, copper chelated compound, magnesium chelated compound, tin chelated compound, and zinc chelated compound. The mineral chelated compound can also include one or more mineral lactate compounds, mineral propionate compounds, mineral butyrate compounds, mineral EDTA compounds, mineral acetate compound, or a combination thereof. Cobalt lactate is one specific example of a mineral chelated compound.

Some organic or inorganic salts particular to this embodiment include salts of aluminum, scandium, selenium, titanium, vanadium, chromium, magnesium, manganese, cobalt, iron, nickel, copper, tin, zinc, molybdenum, or combinations thereof. Suitable salt anions can include bromide, chloride, fluoride, carbonate, hydroxide, nitrate, oxide, phosphate, sulfate, formate, acetate, propionate, butyrate, oxalate, citrate, malate, lactate, or tartrate. Cobalt sulfate is one specific example of an inorganic mineral salt.

Further embodiments of such general mineral complexes include one or more of a carrier, soluble fiber, and enzymes.

Examples of such compounds and methods of making are described in co-owned U.S. patent application Ser. No. 12/835,545, the disclosure of which is herein incorporated by reference.

In some embodiments, the treatment compositions disclosed herein can further comprise one or more commercial seed, soil, or plant treatment compositions. For example, compositions disclosed herein can be combined with QUICK ROOTS® manufactured by TJ Technologies, Inc. In other embodiments compositions disclosed herein can be combined with Optimize® 400 manufactured by Novozymes or INOVATE® manufactured by Valent.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

In the examples, application rates such as 15 g/a indicate an application of 15 g per acre, or 15 g per about 50 lbs of seed. Essential oil application rates given in ppm indicate the weight of oils per weight of seeds. For example, 50 ppm EO indicates that the EO comprises 0.005 wt. % of the combined seeds and EOs.

Commence refers to a seed treatment micronutrient package which has the following composition:

| Commence for Soy/Corn | |
| --- | --- |
| Ingredient | wt. % |
| R.O. Water | 67.13 |
| Lactic Acid | 2.934 |
| Cobalt Carbonate Basic, Monohydrate (50.5% Co) | 1.196 |
| Cobalt Sulfate, Heptahydrate (20.965% Co) | 9.18 |
| Ferric Sodium EDTA (13.26% Fe) | 9.380545 |
| Manganese Lactate, Dihydrate (20.42% Mn) | 3.989777 |
| Copper Sulfate, Pentahydrate (25.46% Cu) | 2.33984 |
| Zinc Sulfate, Monohydrate (36% Zn) | 1.41026 |
| Molybdic Acid (59.2% Mo) | 0.010594 |
| Enzyme W | 0.010594 |
| Larafeed Liquid | 0.941497 |
| Saponix 5000 | 2.809926 |

| Commence for Wheat | |
| --- | --- |
| Ingredient | wt. % |
| R.O. Water | 90.869 |
| Lactic Acid | 1 |
| Cobalt Carbonate Basic, Monohydrate (50.5% Co) | 0.403 |
| Cobalt Sulfate, Heptahydrate (20.965% Co) | 2 |
| Ferric Sodium EDTA (13.26% Fe) | 2.71 |
| Manganese Lactate, Dihydrate (20.42% Mn) | 0.75 |
| Copper Sulfate, Pentahydrate (25.46% Cu) | 0.68 |
| Zinc Sulfate, Monohydrate (36% Zn) | 0.49 |
| Molybdic Acid (59.2% Mo) | 0.004 |
| Enzyme W | 0.004 |
| Larafeed Liquid | 0.28 |
| Saponix 5000 | 0.81 |

Commence for Wheat has a total solids content of about 10% (i.e., about 90% water) due to the water content in Liquid AG and Saponix 5000. Similarly, Commence for Soy and Corn has a total solids content of about 33% (i.e., about 67% water) due to the water content in Liquid AG and Saponix 5000.

Commence is used as a seed treatment by applying the solution to the surface of the seeds. Generate refers micronutrient package with the same formula as Commence, which is applied to a seed, soil, or plant during or after planting. Generate can be applied foliar, in-furrow, or side-dressed, for example.

Essential oil treatments were developed by emulsifying one or more of oregano essential oil, thyme essential oil, and/or synthetic cinnamaldehyde with one of two emulsifiers, ActiFibe (e.g. arabinogalactan) or Tannin (sweet chestnut extract). The notation XD indicates arabinogalactan as the emulsifier, while the notation TD indicates tannic acid as the emulsifier. RALCO SELECT 4XL (SEL OR EO2) refers to an emulsion of essential oils (about 18.75 wt. %), water (about 67.9 wt. %), an emulsifier (about 12.75 wt. %) and TIC gum (less than 1%). The essential oils fraction comprised 66.66% thyme oil (approximately 0.13% wt. % carvacrol, 30.5 wt. % thymol, 18.0 wt. % para-cymene, 18.0 wt. % other secondary thyme oil constituents) and 33.33% synthetic cinnamaldehyde.

REGANO 4XL (REG OR EO1) refers to a similar formula as RALCO SELECT 4XL, but with essential oils of thyme and oregano, wherein the essential oils fraction comprised 50% oregano oil and 50% thyme oil (approximately 60.4 wt. % carvacrol, 10.8 wt. % thymol, 9.9 wt. % paracymene, and 18.9 secondary oil constituents from oregano oil and thyme oil). In the examples, REGANO 4XL TD can be referred to as "EO1".

INOVATE® refers to the commercially available fungicide seed treatment manufactured by Valent Technologies and has the following composition:

| Active Ingredients | By Wt |
| --- | --- |
| Clothianidin[1] | 14.340% |
| Metalaxyl[2] | 1.153% |
| Ipconazole[3] | 0.720% |
| Other Ingredients | 83.787% |

[1](E)-1-(2-chloro-1,3-thiazol-5-ylmethyl)-3-methyl-2-nitroguanidine
[2]N-(2,6-dimethylphenyl)-N-(methoxyacetyl)-DLalaninate
[3]2-[(4-chlorophenyl)methyl]-5-(1-methylethyl)-1-(1H-1,2,4-triazol-1-ylmethyl) cyclopentanol

Example 1: Greenhouse Soy EO1 Seed Treatment

In this trial, soybeans were treated with INOVATE, Commence, essential oils, and combinations thereof, and grown in a greenhouse against untreated checks. In this Example, Commence was applied at a rate of 15 g/a. The variety of soybean treatments allowed for positive controls in addition to the untreated checks (negative controls). Ten seeds from each of the treatments were selected at random from the total amount of seeds treated and were planted individually in 8 inch diameter pots. The pots were placed on tables in a climate and light-controlled greenhouse. Soil for the pots was 75:25 field soil to washed sand mixed very thoroughly in a cement mixer. Plants were watered 3-times per week and were allowed to emerge naturally and taken to pods/beans. FIGS. 3A-D illustrate total pod weight per number of plants, total number of seeds per number of plants, average plant weight (i.e., biomass), and average number of pods per plant, respectively. The addition of essential oils to the soybean seed treatment significantly increased plant performance, and these results suggest that the field yield per acre can be significantly increased as well. The effect of essential oil containing compositions on plant health and growth demonstrated in a greenhouse environment provides evidence of benefit beyond other incidental functions of the essential oils, such as pesticidal functions.

Example 2: Field Soy EO1 Seed Treatment

Figure 4A:
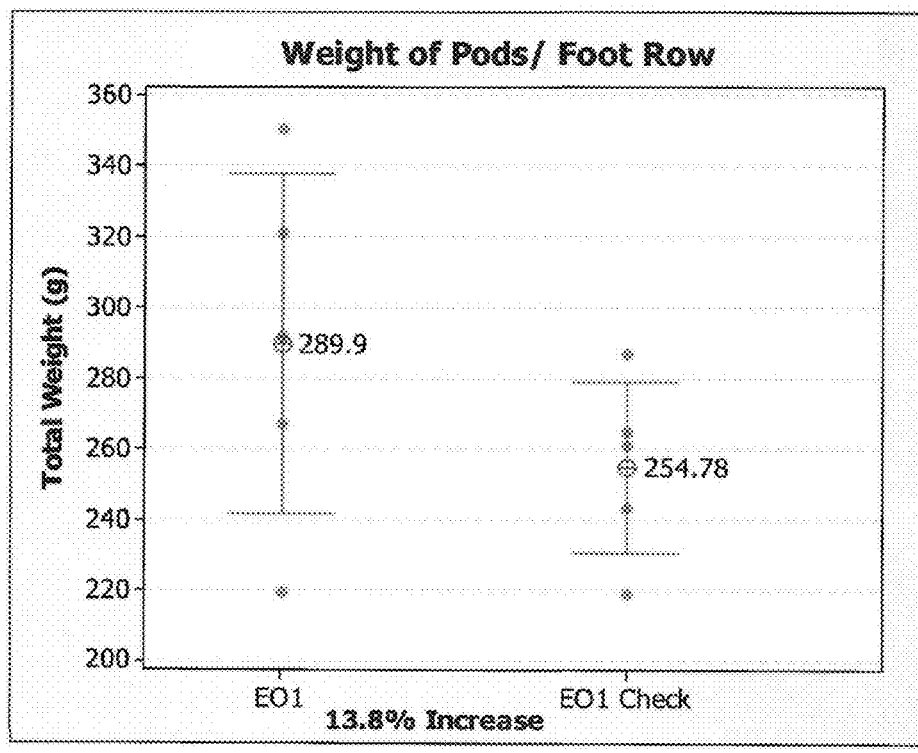
FIGS. 4A-B illustrate yield results from a soy bean field study using essential oil compositions, according to one or more embodiments.
Figure 4B:
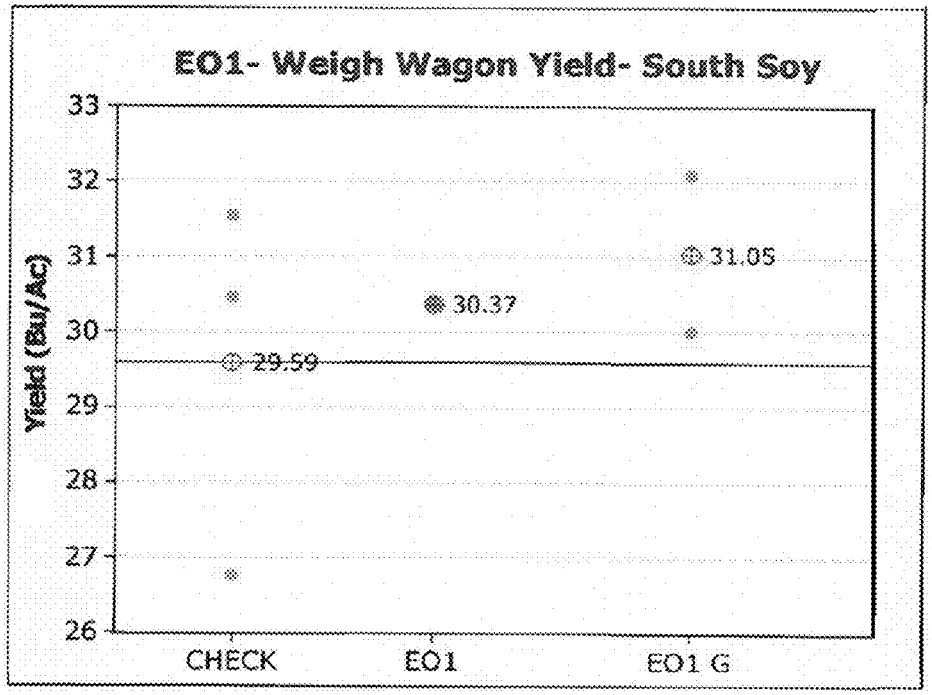

In one study, soybeans treated with EO1 were planted in a field along with an untreated check. FIG. 4A illustrates a marked increase in weight of pods per foot row for soy plants treated with EO1 versus those seeds which were untreated. In another study, soybeans were planted which were treated with EO1, treated with EO1 in combination with Generate applied at 1 pt./acre (i.e., 1 pt. per 50 lbs of seeds) and left untreated as a check. FIG. 4B illustrates yield results for the resulting soy plants. It can be seen that soybeans treated with EO1 outperformed the check, while soybeans treated with EO1 and Generate performed best overall.

Example 3: Field Corn Seed Treatment

Figure 5:
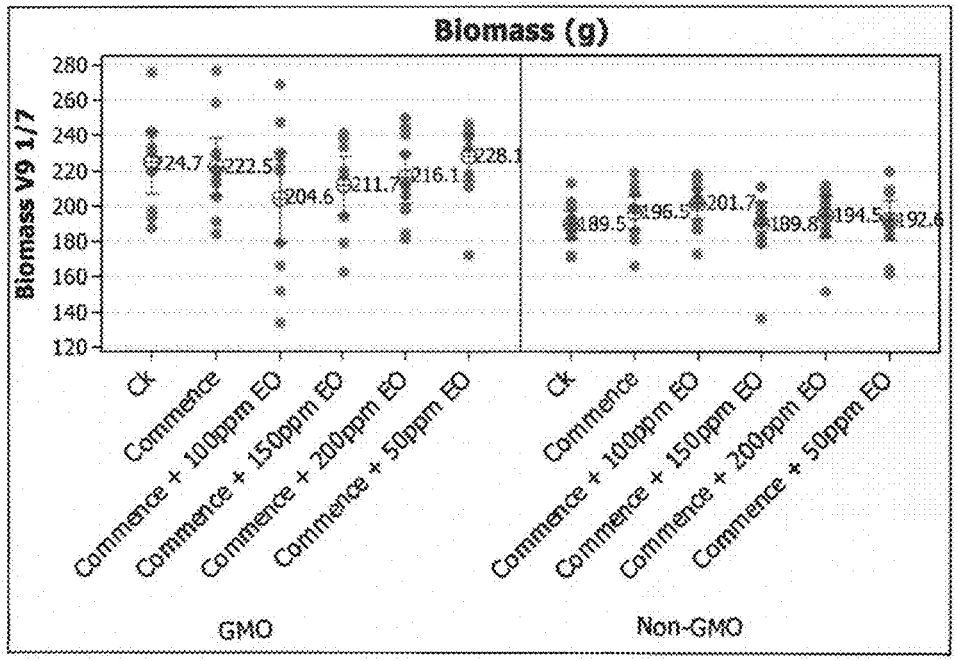
FIG. 5 illustrates results from a field corn study using essential oil compositions, according to one or more embodiments.

In this trial, GMO and non-GMO corn seeds were treated with Commence at 15 g/a, and additionally Commence at 15 g/a in combination with various concentrations of EO1 varying from 50 ppm to 200 ppm. The planting procedure for the corn trail was the same as for used for soybeans in Example 2, wherein treated corn seeds were planted (at 1.5 inches deep, twice the depth of soybean planting), watered under controlled conditions, monitored for growth and health with measurements taken routinely and allowed to grow until the desired end point. Biomass data of plants grown from treated and untreated seeds is illustrated in FIG. 5. In the figure, "EO" refers to the EO1 essential oil formulation.

Example 4: Greenhouse Corn Seed Treatment

Figure 6:
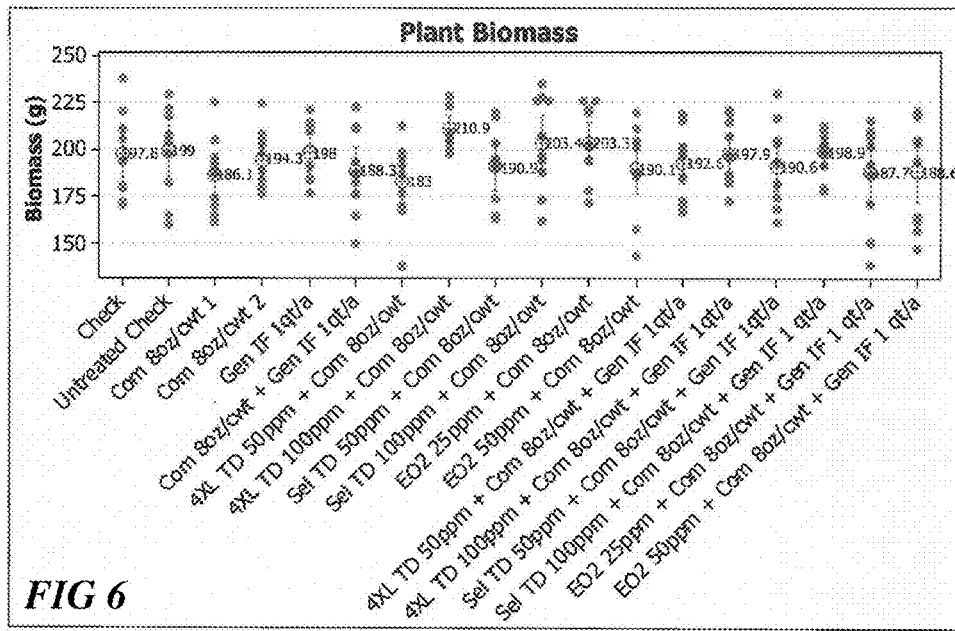
FIG. 6 illustrates results from greenhouse corn study using essential oil compositions, according to one or more embodiments.

In this trial, GMO corn seeds were treated with Commence at 8oz/cwt (i.e., 4 oz/acre), essential oils, and combinations thereof. Ten seeds from each of the pre-treatments were selected at random from the total amount of seeds treated and were planted individually in 8 inch diameter pots. The pots were placed on tables in a climate and light-controlled greenhouse. Soil for the pots was 75:25 field soil to washed sand mixed very thoroughly in a cement mixer. Plants were watered 3-times per week and were allowed to emerge naturally. Some planted seeds were later treated with Generate in-furrow at 1 qt./acre. Untreated seeds were planted as checks. Biomass data for all treatments and checks is illustrated in FIG. 6. The top two performing seed treatments included REGANO 4XL TD and RALCO SELECT 4XL TD, each in combination with Commence. The effect of essential oil containing compositions on plant health and growth demonstrated in a greenhouse environment provides evidence of benefit beyond other incidental functions of the essential oils, such as pesticidal functions.

Example 5: Fungal Inhibition

Figure 7A:
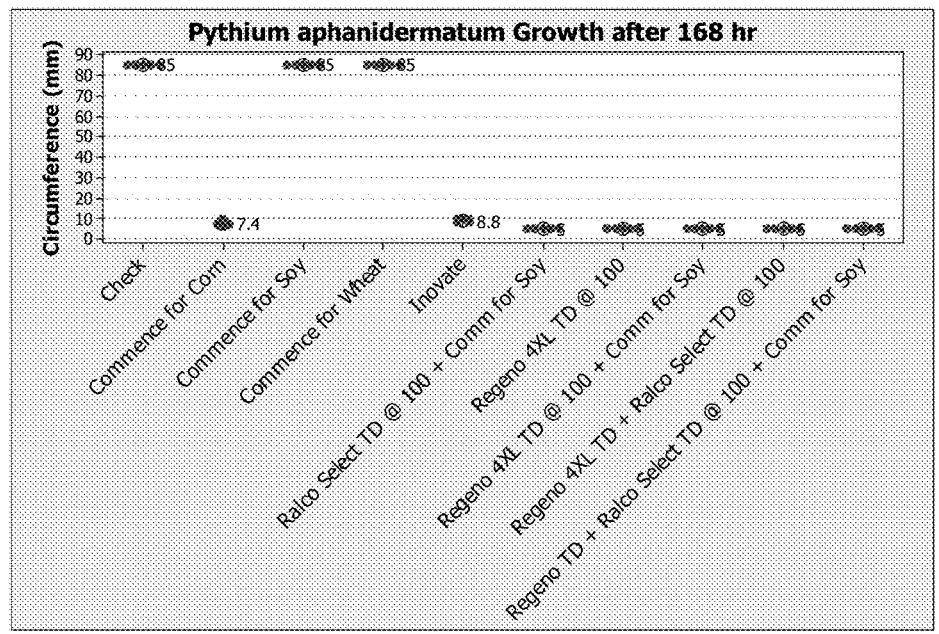
FIGS. 7A-B illustrate circumferential growth of fungal pathogens to demonstrate fungal inhibition properties of essential oil and micronutrient compositions, according to one or more embodiments.
Figure 7B:
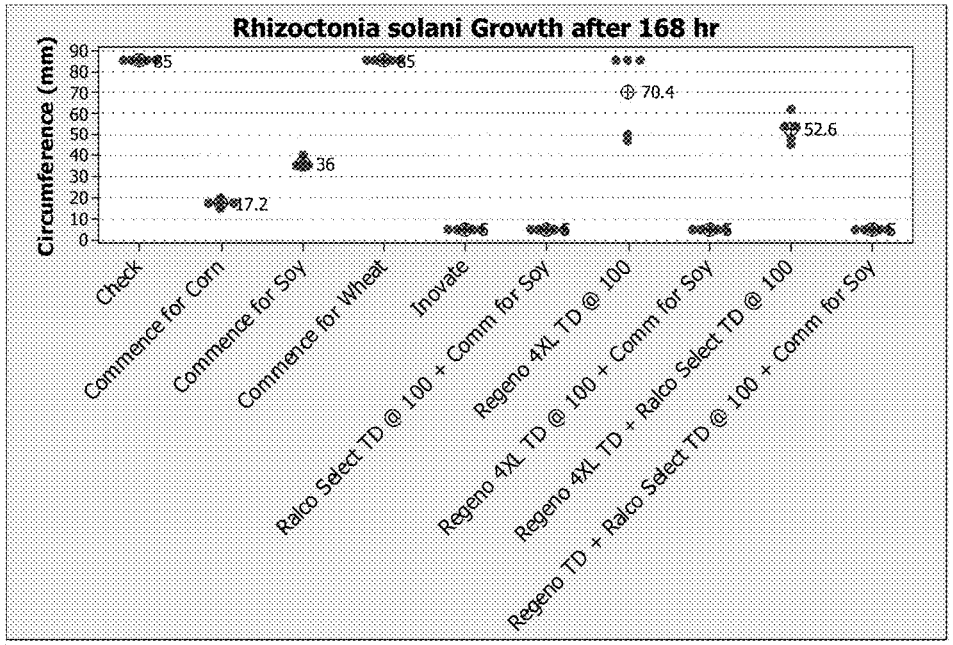

In this trial, Commence, Innovate, EO blends, and combinations thereof were tested to determine their fungal inhibitory ability against *Pythium aphanidermatum* (a pre-emergence pathogenic fungi), and *Rhizoctonia solani* (a post-emergente pathogenic fungi). Each pathogen was plugged onto the surface of applicable agar medium and grown out. 5 mm mycelial plugs were removed from the leading colony edge and placed mycelial side down onto the fungicide amended agar medium (either Potato Dextrose Agar or Corn Meal Agar) for evaluation. Circumference of the mycelial growth was measured every 24 hours. EO blends were applied at 100 ppm relative to the agar. Commence labeled soy and wheat was applied at a rate of 2 oz./50 lbs of agar, while Commence labeled corn was applied at twice that rate at of 4 oz./50 lbs of agar. Circumferential growth of *Pythium aphanidermatum* at 168 hrs is shown in FIG. 7A and Circumferential growth of *Rhizoctonia solani* at 168 hrs is shown in FIG. 7B. The difference in fungal inhibition between commence for corn, commence for soy, and commence for wheat can be explained by the difference in formulations (higher solids content of Commence for corn/soy) and the application rates within this trial. The results in FIGS. 7A-B show promise for Commence and EO blends for use as fungicides.

What is claimed is:

1. A seed, soil, or plant treatment composition, the composition comprising:
   one or more emulsifiers, wherein the one or more emulsifiers include at least arabinogalactan; and
   one or more essential oils, wherein the one or more essential oils include at least cinnamon essential oil;
   wherein the one or more essential oils are present as an emulsion and the average particle size of the one or more essential oils in the emulsion is less than or about 25 microns.

2. The composition of claim 1, wherein the one or more emulsifiers further comprise a tannin compound.

3. The composition of claim 1, wherein the one or more essential oils further comprise one or more of oregano essential oil, thyme essential oil, and combinations thereof.

4. The composition of claim 1, wherein the cinnamon essential oil comprises synthetic cinnamaldehyde.

5. The composition of claim 1, wherein the one or more essential oils further comprise one or more of oregano essential oil, thyme essential oil, lavender essential oils, Mexican bay leaf essential oils, West Indian bay tree essential oils, Indonesian bay leaf essential oils, bay laurel essential oils, California bay laurel essential oils, lemon grass essential oils, spearmint essential oils, peppermint essential oils, rosemary essential oils, sage essential oils, anise essential oils, ginger essential oils, bergamot essential oils, *eucalyptus* essential oils, *melaleuca* essential oils, *cannabis* essential oils, marjoram essential oils, orange essential oils, and rose essential oils.

6. The composition of claim 1, further comprising one or more metals; wherein the one or more metals include aluminum, iron, cobalt, magnesium, tin, manganese, zinc, copper, scandium, selenium, titanium, vanadium, chromium, and nickel.

7. The treatment composition of claim 6, wherein the one or more metals are present as a salt, a chelated compound, or combinations thereof.

8. A seed, soil, or plant treatment composition, the composition comprising:
   one or more essential oils, wherein the one or more essential oils include at least cinnamon essential oil and optionally one or more of thyme essential oil and oregano essential oil;
   one or more emulsifiers, wherein the one or more emulsifiers include at least arabinogalactan; and
   a metal chelated compound;
   wherein the one or more essential oils are present as an emulsion and the average particle size of the one or more essential oils in the emulsion is less than or about 25 microns.

9. The composition of claim 8, wherein the one or more metals include aluminum, iron, cobalt, magnesium, tin, manganese, zinc, copper, scandium, selenium, titanium, vanadium, chromium, or nickel.

10. The composition of claim 8, wherein the chelant of the metal chelated compound is one of lactate, acetate, propionate, butyrate, ethylene diamine, or EDTA.

11. The composition of claim 8, wherein the one or more emulsifiers further comprise a tannin compound.

12. A seed, soil, or plant treatment composition, the composition comprising:
   synthetic cinnamaldehyde;
   one or more essential oils from the Lamiaceae family; and
   one or more emulsifiers, wherein the one or more emulsifiers include at least arabinogalactan;
   wherein the one or more essential oils are present as an emulsion and the average particle size of the one or more essential oils in the emulsion is less than or about 25 microns.

13. The composition of claim 12, wherein the one or more essential oils from the Lamiaceae family comprise essential oils from the *Thymus* genus, the *Origanum* genus, or combinations thereof.

14. The composition of claim 12, wherein essential oils from the Lamiaceae family further comprise essential oils from the *Lavandula* genus, the *Mentha* genus, the *Rosmarinus* genus, and the *Salvia* genus.

15. The composition of claim 12, further comprising one or more essential oils from the *Liteas* genus, the *Pimenta* genus, the *Syzygium* genus, the *Laurus* genus, the *Umbellularia* genus, the *Cymbopogon* genus, the *Pimpinella* genus, the *Zingiber* genus, the *Citrus* genus, the *Eucalyptus* genus, the *Melaleuca* genus, the *Gaultheria* genus, the *Cannabis* genus, the *Citrus* genus, and the *Rosa* genus.

16. The composition of claim 12, further comprising a metal chelated compound.

17. The composition of claim 16, wherein the metal of the metal chelated compound include one or more of aluminum, iron, cobalt, magnesium, tin, manganese, zinc, copper, scandium, selenium, titanium, vanadium, chromium, and nickel; wherein the chelant of the metal chelated compound is one of lactate, acetate, propionate, butyrate, ethylene diamine, or EDTA.

18. The composition of claim 12, wherein the one or more emulsifiers further comprise a tannin compound.

19. A method of treating a seed, soil, or plant, the method comprising:
   applying a treatment composition to one or more of a seed, soil, and a plant,
   wherein the treatment composition comprises one or more essential oils and one or more emulsifiers, wherein the one or more essential oils include at least cinnamon essential oil, wherein the one or more emulsifiers include at least arabinogalactan, wherein the one or more essential oils are present as an emulsion and the average particle size of the one or more essential oils in the emulsion is less than or about 25 microns.

20. The method of claim 19, wherein the one or more essential oils further comprise one or more of thyme essential oil and oregano essential oil.

21. The composition of claim 19, wherein the cinnamon essential oil comprises synthetic cinnamaldehyde.

22. The composition of claim 19, wherein the cinnamon essential oil comprises synthetic cinnamaldehyde and the one or more essential oils further comprise one or more essential oils from the Lamiaceae family.

23. The method of claim 19, wherein the seed comprises a seed intended for planting or agricultural purposes.

24. The method of claim 19, wherein the one or more emulsifiers further comprise a tannin compound.

25. A method of treating a seed, soil, or plant to increase the health of seeds and growing plants, the method comprising:
   applying a treatment composition to one or more of a seed, soil, and a plant, wherein the treatment composition comprises one or more essential oils and one or more emulsifiers, wherein the one or more emulsifiers includes at least arabinogalactan;
   wherein the one or more essential oils comprise at least cinnamon essential oil and optionally one or more of thyme essential oil and oregano essential oil, and increasing the health of seeds and growing plants can include enhancing yield, germination rate, growth, nutrient uptake and retention, drought resistance, and temporal bio-availability of nutrients in and around a seed or plant wherein the one or more essential oils are present as an emulsion, and the average particle size of the one or more essential oils in the emulsion is less than or about 25 microns.

26. The composition of claim 25, further comprising one or more pesticides.

27. The method of claim 25, wherein increasing the health of a seed, soil, and plant further includes deterring fungal propagation.

28. The method of claim 25, wherein the one or more emulsifiers further comprise a tannin compound.

* * * * *